(12) United States Patent
Kazmierczak et al.

(10) Patent No.: US 7,867,183 B2
(45) Date of Patent: Jan. 11, 2011

(54) KNEE BRACE HAVING A RIGID FRAME AND PATELLOFEMORAL SUPPORT

(75) Inventors: Andy Kazmierczak, Vista, CA (US); John Martin, Oceanside, CA (US); Richard E. Gildersleeve, Carlsbad, CA (US); John Fulkerson, Harford, CT (US); Kurt Jacobson, Hamilton, GA (US); Scott Seligman, San Marcos, CA (US)

(73) Assignee: DJ Orthopedics, LLC, Vista, CA (US)

( * ) Notice: Subject to any disclaimer, the term of this patent is extended or adjusted under 35 U.S.C. 154(b) by 762 days.

(21) Appl. No.: 11/529,743

(22) Filed: Sep. 28, 2006

(65) Prior Publication Data

US 2008/0208095 A1 Aug. 28, 2008

Related U.S. Application Data

(60) Provisional application No. 60/722,739, filed on Sep. 30, 2005.

(51) Int. Cl.
*A61F 5/00* (2006.01)
(52) U.S. Cl. .................................. 602/26; 602/5; 602/23
(58) Field of Classification Search ...................... 602/5, 602/16, 26, 60–64, 23
See application file for complete search history.

(56) References Cited

U.S. PATENT DOCUMENTS

| | | | |
|---|---|---|---|
| 3,473,527 A | 10/1969 | Spiro | |
| 3,581,741 A * | 6/1971 | Rosman et al. | 602/16 |
| 3,786,804 A | 1/1974 | Lewis | |
| 3,804,084 A | 4/1974 | Lehman | |
| 3,817,244 A | 6/1974 | Taylor | |
| 3,945,046 A | 3/1976 | Stromgren | |
| 4,064,874 A | 12/1977 | Valin | |
| 4,116,236 A | 9/1978 | Albert | |
| 4,201,203 A | 5/1980 | Applegate | |
| 4,287,884 A | 9/1981 | Applegate | |
| 4,287,885 A | 9/1981 | Applegate | |

(Continued)

FOREIGN PATENT DOCUMENTS

DE 1024204 2/1958

(Continued)

*Primary Examiner*—Kim M Lewis
(74) *Attorney, Agent, or Firm*—Ropes & Gray LLP

(57) ABSTRACT

Embodiments of the knee brace disclosed herein provide a combination of external ligament support and/or relief from pain caused by osteoarthritis with patellofemoral support. The brace includes a rigid frame and a flexible strap configured to extend across the wearer's patella to provide anterior loading thereto. The strap is operatively secured at either end to components of the rigid frame, thereby providing maximum leverage for applying force to the wearer's patella. In some embodiments, the strap includes a removable and adjustable buttress for directly contacting the wearer's patella. The patellar strap provides dynamic loading to the patella through the wearer's range of motion for relief of patellofemoral dysfunction, such as patellar shift, subluxation and dislocation, and malalignments such as patella alta, patella baja, tilt and glide. In some embodiments, a conversion kit is provided for converting a rigid brace frame into a knee brace capable of providing patellofemoral support to a wearer's knee. The kit includes at least a patellar strap and at least one tab for securing the strap to the rigid frame.

26 Claims, 13 Drawing Sheets

U.S. PATENT DOCUMENTS

| | | |
|---|---|---|
| 4,296,744 A | 10/1981 | Palumbo |
| 4,353,362 A | 10/1982 | DeMarco |
| 4,366,813 A | 1/1983 | Nelson |
| 4,370,978 A | 2/1983 | Palumbo |
| 4,378,009 A | 3/1983 | Rowley et al. |
| 4,445,505 A | 5/1984 | Labour et al. |
| 4,651,722 A | 3/1987 | Karczewski |
| 4,697,583 A | 10/1987 | Mason et al. |
| 4,700,698 A | 10/1987 | Kleylein |
| 4,872,448 A | 10/1989 | Johnson, Jr. |
| 4,887,590 A | 12/1989 | Logue et al. |
| 4,938,207 A | 7/1990 | Vargo |
| 4,941,462 A | 7/1990 | Lindberg |
| 4,986,263 A | 1/1991 | Dickerson et al. |
| 5,016,621 A | 5/1991 | Bender |
| 5,024,216 A | 6/1991 | Shiono |
| 5,036,837 A | 8/1991 | Mitchell et al. |
| 5,042,464 A * | 8/1991 | Skwor et al. .................. 602/16 |
| 5,139,476 A | 8/1992 | Peters |
| 5,139,477 A | 8/1992 | Peters |
| 5,221,252 A | 6/1993 | Caprio, Jr. et al. |
| 5,261,871 A | 11/1993 | Greenfield |
| 5,267,951 A | 12/1993 | Ishii |
| 5,277,697 A | 1/1994 | France et al. |
| 5,334,135 A | 8/1994 | Grim et al. |
| 5,383,843 A | 1/1995 | Watson et al. |
| 5,385,538 A | 1/1995 | Mann |
| 5,399,153 A | 3/1995 | Caprio, Jr. et al. |
| 5,411,037 A | 5/1995 | Hess et al. |
| 5,417,646 A | 5/1995 | Gauvry |
| 5,419,161 A | 5/1995 | Bodenschatz et al. |
| 5,451,201 A | 9/1995 | Prengler |
| 5,462,517 A | 10/1995 | Mann |
| 5,472,413 A | 12/1995 | Detty |
| 5,512,039 A | 4/1996 | White |
| 5,527,267 A | 6/1996 | Billotti |
| 5,554,105 A | 9/1996 | Taylor |
| 5,599,288 A | 2/1997 | Shirley et al. |
| 5,626,557 A | 5/1997 | Mann |
| 5,695,452 A | 12/1997 | Grim et al. |
| 5,711,312 A | 1/1998 | Staudinger |
| 5,759,167 A | 6/1998 | Shields et al. |
| 5,792,084 A | 8/1998 | Wilson et al. |
| 5,797,864 A | 8/1998 | Taylor |
| 5,807,298 A | 9/1998 | Palumbo |
| 5,873,848 A | 2/1999 | Fulkerson |
| 6,238,360 B1 | 5/2001 | Gildersleeve et al. |
| 6,287,269 B1 | 9/2001 | Osti et al. |
| 6,336,909 B2 | 1/2002 | Gildersleeve et al. |
| 6,551,264 B1 * | 4/2003 | Cawley et al. ................. 602/16 |
| 7,060,045 B2 * | 6/2006 | Mason et al. .................. 602/5 |
| 2004/0054307 A1 | 3/2004 | Mason et al. |
| 2004/0153017 A1 | 8/2004 | Simmons et al. |

FOREIGN PATENT DOCUMENTS

| | | |
|---|---|---|
| DE | 27 24 586 A1 | 12/1978 |
| DE | 35 11 250 A1 | 7/1985 |
| DE | 4013693 | 8/1991 |
| EP | 0 290 409 A1 | 11/1988 |
| EP | 0 809 478 B1 | 12/1997 |
| FR | 2486388 | 1/1982 |
| FR | 2807644 | 10/2001 |
| GB | 2136294 | 9/1984 |
| WO | WO 00/51537 | 9/2000 |

* cited by examiner

KNEE BRACE HAVING A RIGID FRAME AND PATELLOFEMORAL SUPPORT

CROSS-REFERENCE TO RELATED APPLICATION

This application claims priority to provisional application Ser. No. 60/722,739, filed on Sep. 30, 2005, the entire contents of which are hereby incorporated by reference.

BACKGROUND OF THE INVENTION

1. Field of the Invention

The present invention relates generally to orthotic devices, and more specifically to knee braces for, for example, supporting ligament instability and/or treating patellofemoral dysfunction.

2. Description of the Related Art

Many orthotic devices support and/or protect the joints of the human anatomy, such as the knee joint. For instance, a wide variety of knee braces are generally intended to limit unnatural knee joint movement, which is a common source of structural damage to the knee. At the same time, such knee braces preferably allow a natural range of knee motion so as not to impede normal walking, running or other knee movements.

Knee braces are also commonly used to prevent or remediate functional disorders of the patellofemoral joint. The patellofemoral joint of the knee is an articulation between the patella and femur. The joint includes an articular surface on the posterior of the patella and a corresponding articular surface on the anterior of the head of the femur that is termed the trochlea. The posterior of the patella is contoured as a ridge, while the trochlea is contoured as a groove that is dimensioned to receive the patellar ridge in a complementary manner. In a healthy patellofemoral joint, the patellar ridge accurately tracks the underlying trochlear groove as the knee is moved through flexion or extension.

The patellofemoral joint is subject to a wide variety of functional disorders that adversely affect the joint operation. Less severe forms of patellofemoral joint disorder cause pain in the joint, but do not exhibit errors in patellar tracking of the trochlear groove. In more severe forms of patellofemoral joint disorder, patellar tracking errors are evident in addition to joint pain, but there is no subluxation or dislocation of the joint. In still more severe forms of patellofemoral joint disorder, patellar tracking errors result in subluxation or dislocation of the joint. Recurrent subluxation of the patellofemoral joint is a particular disorder whereby the patella deviates transiently and typically rapidly from its normal axis of movement due to patellar tracking errors during movement of the knee. Slight deviations of the patella from its normal axis of movement are termed minor subluxation and often do not produce clinically apparent relocation of the patella. Minor subluxation is often the result of a functional imbalance in the knee. Significant deviations of patellar movement that approach dislocation are termed major subluxation. In certain instances, major subluxation is induced by strenuous activity, although it often occurs even in the absence of such activity. Recurrent patellar subluxation, both major and minor, is a relatively frequent condition among females generally and among female athletes in particular.

Many instances of subluxation or dislocation of the patella due to patellar tracking errors are in the lateral direction because biomechanical forces typically bias the patella laterally when the knee is load-bearing. Additionally, subluxation or dislocation of the patella due to patellar tracking errors has the greatest risk of occurring when the knee is approaching extension. Specifically, when the knee ranges between about 30° of full extension and full extension, the trochlear groove becomes relatively small and shallow which is conducive to subluxation or dislocation. Functional disorders of the patellofemoral joint are highly disadvantageous because such disorders often ultimately lead to cartilage damage and arthritis of the knee.

SUMMARY OF THE INVENTION

The preferred embodiments of the present knee brace having a rigid frame and patellofemoral support have several features, no single one of which is solely responsible for their desirable attributes. Without limiting the scope of this knee brace as expressed by the claims that follow, its more prominent features will now be discussed briefly. After considering this discussion, and particularly after reading the section entitled "Detailed Description of the Preferred Embodiments," one will understand how the features of the preferred embodiments provide advantages, which include the combination of rigid brace components for providing ligament stability and/or providing relief from osteoarthritis pain and flexible brace components for providing patellofemoral support, support and symptomatic pain relief for patellofemoral dysfunction, including lateral patellar tracking errors, subluxation, dislocation, and patellar tendonitis, and ready conversion of a rigid brace frame into a brace that also provides patellofemoral support.

One embodiment of the present knee brace having a rigid frame and patellofemoral support comprises a knee brace for supporting and/or protecting a wearer's knee, while also providing support to the wearer's patella. The brace comprises a rigid brace frame including a rigid thigh cuff, a rigid calf cuff, and at least a first hinge pivotably securing the thigh cuff to the calf cuff. The brace further comprises a patellar strap having a base portion and at least a first arm extending from the base portion. The base portion is operatively secured to the rigid brace frame along a medial side or a lateral side thereof. The arm extends across an anterior portion of the rigid brace frame and is secured to the rigid brace frame along the medial side or the lateral side thereof, opposite the base portion.

Another embodiment of the present knee brace comprises a kit for converting a knee brace into a knee brace configured for providing patellofemoral support to a knee of a wearer. The kit comprises a patellar strap having a base portion and at least a first elongate arm extending therefrom. The kit further comprises at least a first anchoring member configured to releasably secure the first arm of the patellar strap.

Another embodiment of the present knee brace comprises a method of converting a knee brace having a rigid brace frame into a knee brace capable of providing patellofemoral support to a knee of a wearer. The method comprises the step of securing a base portion of a patellar strap to the frame along a medial side or a lateral side thereof. The strap includes at least a first elongate arm. The method further comprises the step of securing at least a first anchoring member to the medial side or the lateral side of the frame, opposite the base portion.

BRIEF DESCRIPTION OF THE DRAWINGS

The preferred embodiments of the present knee brace having a rigid frame and patellofemoral support, illustrating its features, will now be discussed in detail. These embodiments depict the novel and non-obvious knee brace shown in the accompanying drawings, which are for illustrative purposes only. These drawings include the following figures, in which like numerals indicate like parts.

DETAILED DESCRIPTION OF THE PREFERRED EMBODIMENTS

Embodiments of the present knee brace 20 (FIGS. 1-3) advantageously combine a rigid frame 22 with a patellofemoral support device. The rigid components of the brace 20 may provide support and protection to the wearer's knee in one or more ways. For example, the rigid components may act as external substitutes for damaged knee ligaments and/or prevent injury to healthy knee ligaments. Alternatively, the rigid components may support a knee that has degenerated due to osteoarthritis. The patellofemoral support device provides support and symptomatic pain relief for patellofemoral dysfunction, including lateral mal-tracking, subluxation/dislocation, and patellar tendonitis. The brace 20 can advantageously be used for sports activities (including contact and non-contact sports) and in the activities of daily living.

Figure 1:
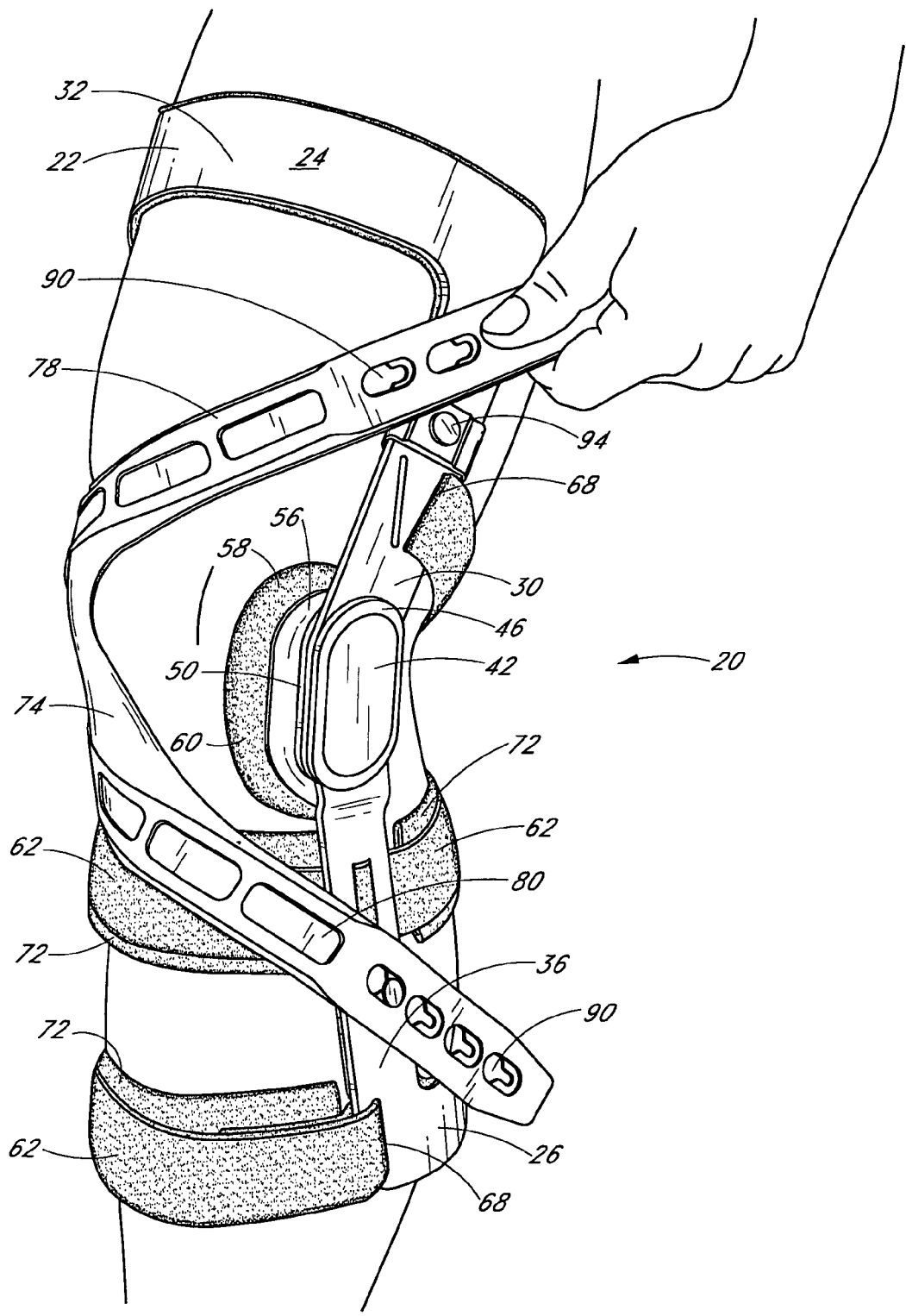
FIG. 1 is a front/medial perspective view of one embodiment of the present knee brace disposed on a wearer's leg.
Figure 2:
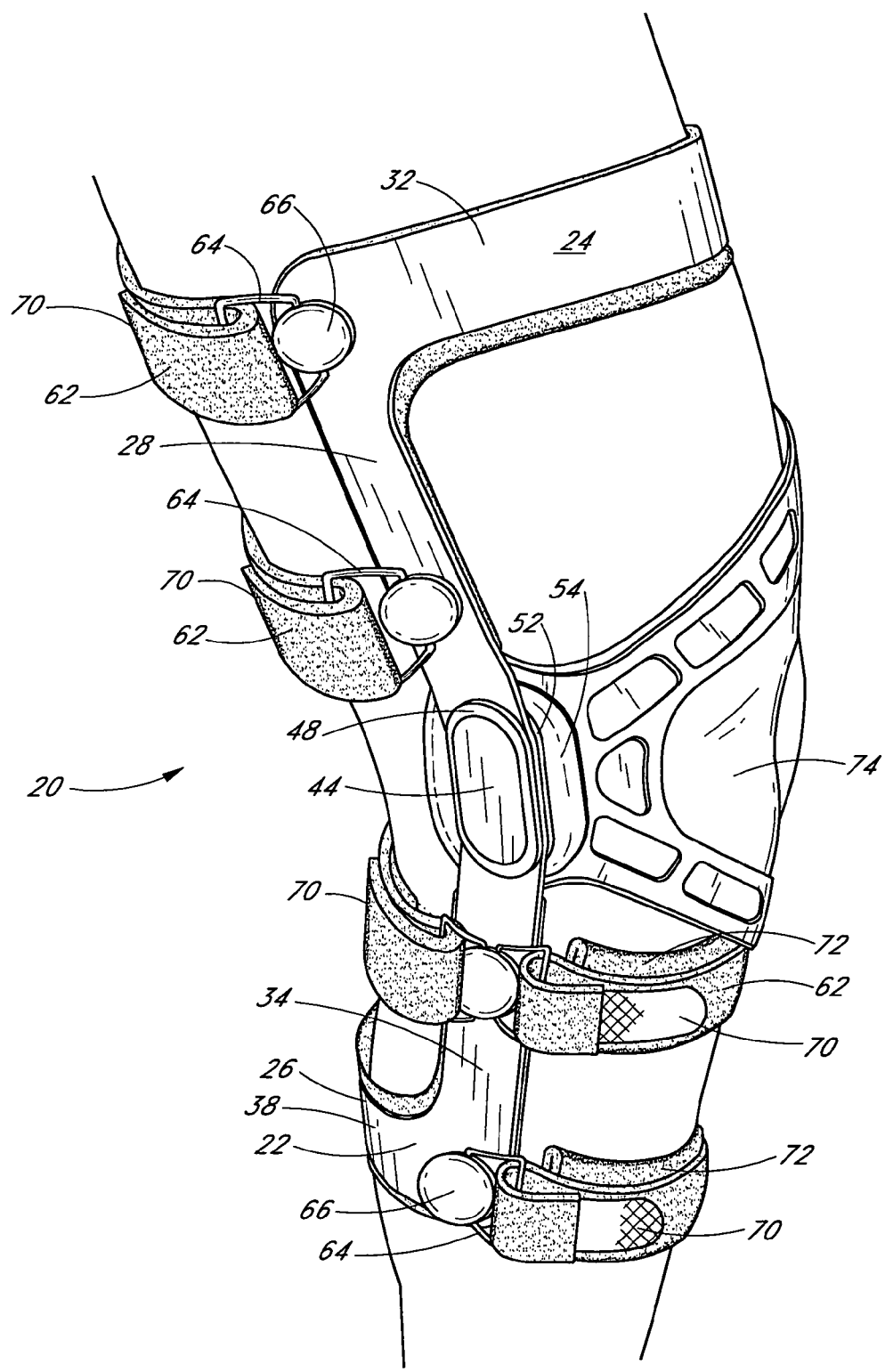
FIG. 2 is a front/lateral perspective view of the brace of FIG. 1 disposed on a wearer's leg.
Figure 3:
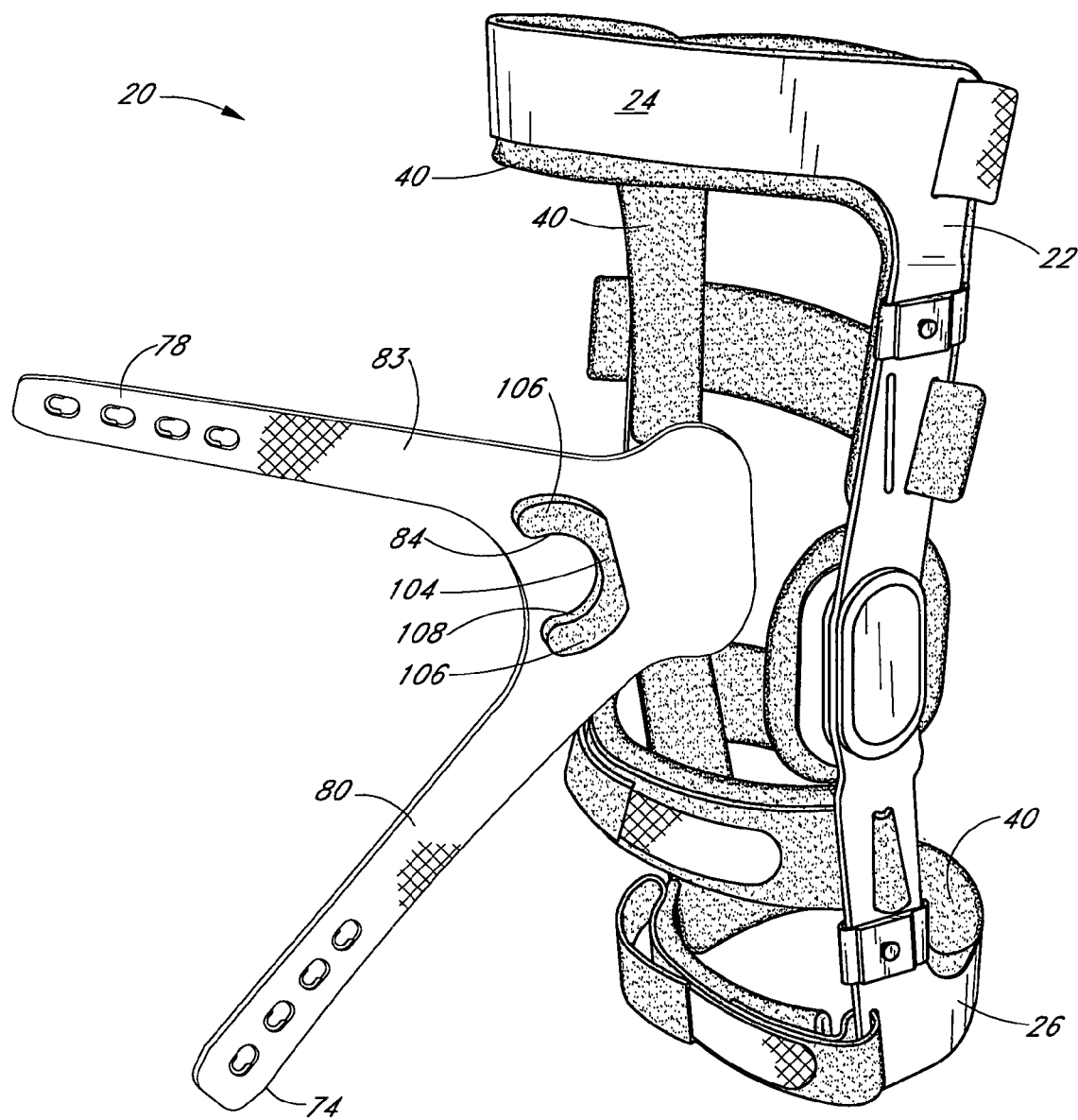
FIG. 3 is a front/medial perspective view of the brace of FIG. 1, illustrating a patellofemoral support device thereof in an extended configuration.

In one embodiment, the brace 20 comprises a rigid frame 22, such as the frame 22 shown in FIGS. 1-3. The frame 22 may be designed to, for example, support a wearer's knee ligaments or relieve pain caused by osteoarthritis. For example, the frame 22 may share many similarities with the braces described in U.S. Pat. Nos. 4,697,583, 6,527,733 and 6,623,439. The disclosure of each of these patents is hereby incorporated by reference.

The frame 22 may include a rigid thigh cuff 24 and a rigid calf cuff 26. In the illustrated embodiments, the thigh cuff 24 includes a substantially straight lateral thigh upright 28 (FIG. 2) that extends along the lateral side of the wearer's thigh, a substantially straight medial thigh upright 30 (FIG. 1) that extends along the medial side of the wearer's thigh, and a curved thigh segment 32 that extends around the anterior of the wearer's thigh. In the embodiment of FIGS. 1 and 2, the curved thigh segment 32 extends substantially straight across the wearer's thigh. However, those of skill in the art will appreciate that the curved thigh segment may extend, for example, first in a substantially straight direction across the wearer's thigh and then diagonally downward before joining the medial thigh upright. U.S. Pat. No. 6,623,439, incorporated by reference herein, discloses a knee brace having such a configuration. Opposite ends of the thigh segment 32 adjoin upper ends of the lateral and medial thigh uprights 28, 30. In the illustrated embodiment, the lateral thigh upright 28, the medial thigh upright 30 and the curved thigh segment 32 are formed integrally. However, those of skill in the art will appreciate that these components could be formed separately and be secured to one another with welds, fastening members, etc.

Similarly to the thigh cuff 24, the calf cuff 26 includes a substantially straight lateral calf upright 34 (FIG. 2) that extends along the lateral side of the wearer's calf, a substantially straight medial calf upright 36 (FIG. 1) that extends along the medial side of the wearer's calf, and a curved calf segment 38 (FIG. 2) that extends around the posterior of the wearer's calf. Opposite ends of the calf segment 38 adjoin lower ends of the lateral and medial calf uprights 34, 36. In the illustrated embodiment, the lateral calf upright 34, the medial calf upright 36 and the curved calf segment 38 are formed integrally. However, those of skill in the art will appreciate that these components could be formed separately and be secured to one another with welds, fastening members, etc.

The thigh and calf cuffs 24, 26 may be constructed of a material that is rigid and lightweight. For example, metals may be used, such as aluminum or titanium. Alternatively, composite materials may be used, such as those including fibers embedded in a polymer matrix. With reference to FIG. 3, the frame 22 may include a padding layer 40 covering some or all of the surfaces of the cuffs 24, 26 that face the wearer's leg. The padding layer 40 provides a comfortable interface between the wearer's leg and the relatively hard cuffs 24, 26. The padding layer 40 may be constructed from, for example, a foam layer sandwiched between fabric layers. The padding layer 40 may be secured to the cuffs using well-known methods, such as hook-and-loop fastener, snaps, etc.

The frame 22 further includes a medial hinge 42 (FIG. 1) and a lateral hinge 44 (FIG. 2). In the illustrated embodiment, each of the hinges is bicentric, although those of ordinary skill in the art will appreciate that the hinges could be monocentric. The medial hinge 42 includes at least a first medial hinge plate 46 (FIG. 1) to which a lower end of the medial thigh upright 30 and an upper end of the medial calf upright 36 are each pivotably secured. Similarly, the lateral hinge 44 includes at least a first lateral hinge plate 48 (FIG. 2) to which a lower end of the lateral thigh upright 28 and an upper end of the lateral calf upright 34 are each pivotably secured. The hinges 42, 44 thus pivotably secure the cuffs 24, 26 to one another. The pivoting engagement between each hinge plate and its respective uprights may comprise, for example, a pair of spaced holes (not shown) in the hinge plate that align with respective holes in the uprights, and fastening members (not shown) that extend through the aligned holes. In the illustrated embodiment, each of the hinges 42, 44 includes a second hinge plate 50, 52, such that each of the uprights is sandwiched between respective first and second hinge plates. Those of skill in the art will appreciate that each hinge 42, 44 may comprise only a first hinge plate, or a first hinge plate and a second hinge plate, and that if only one hinge plate is provided it may be located inside or outside the uprights relative to the wearer's knee.

The ends of each upright may include gear teeth (not shown), such that the teeth on the thigh cuff 24 engage the teeth on the calf cuff 26. As the thigh cuff 24 rotates with respect to the hinges, interengagement of the gear teeth induces rotation of the calf cuff 26, and vice versa. The hinges 42, 44 may include one or more flexion and/or extension stops (not shown) that set maximum angles of flexion and/or extension for the wearer's knee.

With further reference to FIGS. 1 and 2, the present brace 20 further comprises a lateral condylar shell 54 and a medial condylar shell 56. In the illustrated embodiment, each condylar shell 54, 56 is secured to a respective one of the lateral and medial second hinge plates 48, 46. Each condylar shell 54, 56 has a substantially oval-shaped perimeter, and is adapted to receive a condylar pad, such as the pad 58 illustrated in FIG. 1. Each condylar pad 58 has a substantially oval-shaped perimeter, and is adapted to be secured to a respective one of the condylar shells 54, 56. For example, the embodiment of FIGS. 1 and 2 includes a cushioning portion (not visible) and a sleeve portion 60. The cushioning portion is constructed of a compressible material, such as foam, and includes a curved ridge-like protrusion (not shown) along a lower portion thereof that faces the wearer's leg when the brace 20 is worn. The sleeve 60 fits over the cushioning portion and overlaps the edges of the condylar shell 54, 56, trapping the cushioning portion between the sleeve and the shell and securing the condylar pad assembly to the condylar shell. The condylar shell may also include a patch of hook fastener that mates with loop material on the condylar pad.

With reference to FIGS. 1 and 2, a plurality of straps 62 extend around the wearer's lower leg and upper leg to secure the rigid frame 22 to the wearer's leg. Ends of the straps 62 connect to the rigid frame 22. Ends of the straps 62 may include D-rings 64 (FIG. 2) that are received within strap tab caps 66 to secure the straps 62 to the frame 22. In certain embodiments, the strap tab caps 66 may be rotatable with respect to the frame 22. Alternatively, the straps 62 may thread through apertures 90 68 (FIG. 1) in the uprights. In the embodiment of FIGS. 1 and 2, each strap 62 threads through elongate apertures 90 68 in the medial uprights 30, 36 and connects to the lateral uprights 28, 34 via D-rings 64 and strap tab caps 66. Each strap 62 further includes loop fastener on a surface that faces away from the wearer's leg. An end 70 of each strap 62 threads through its respective D-ring 64 and folds back over the strap 62, as shown in FIG. 2. Hook fastener (not shown) on the strap end 70 engages the loop fastener on the intermediate portion of the strap 62 to secure the strap end 70. Each strap 62 may further include padding material 72 secured to a surface thereof that faces the wearer's leg. The padding 72 provides a comfortable interface between the strap 62 and the wearer's leg. However, those of skill in the art will appreciate that the padding 72 need not be provided. The padding 72, if provided, may be integral with the strap 62, or secured thereto, such as by hook-and-loop fastener.

Figure 4:
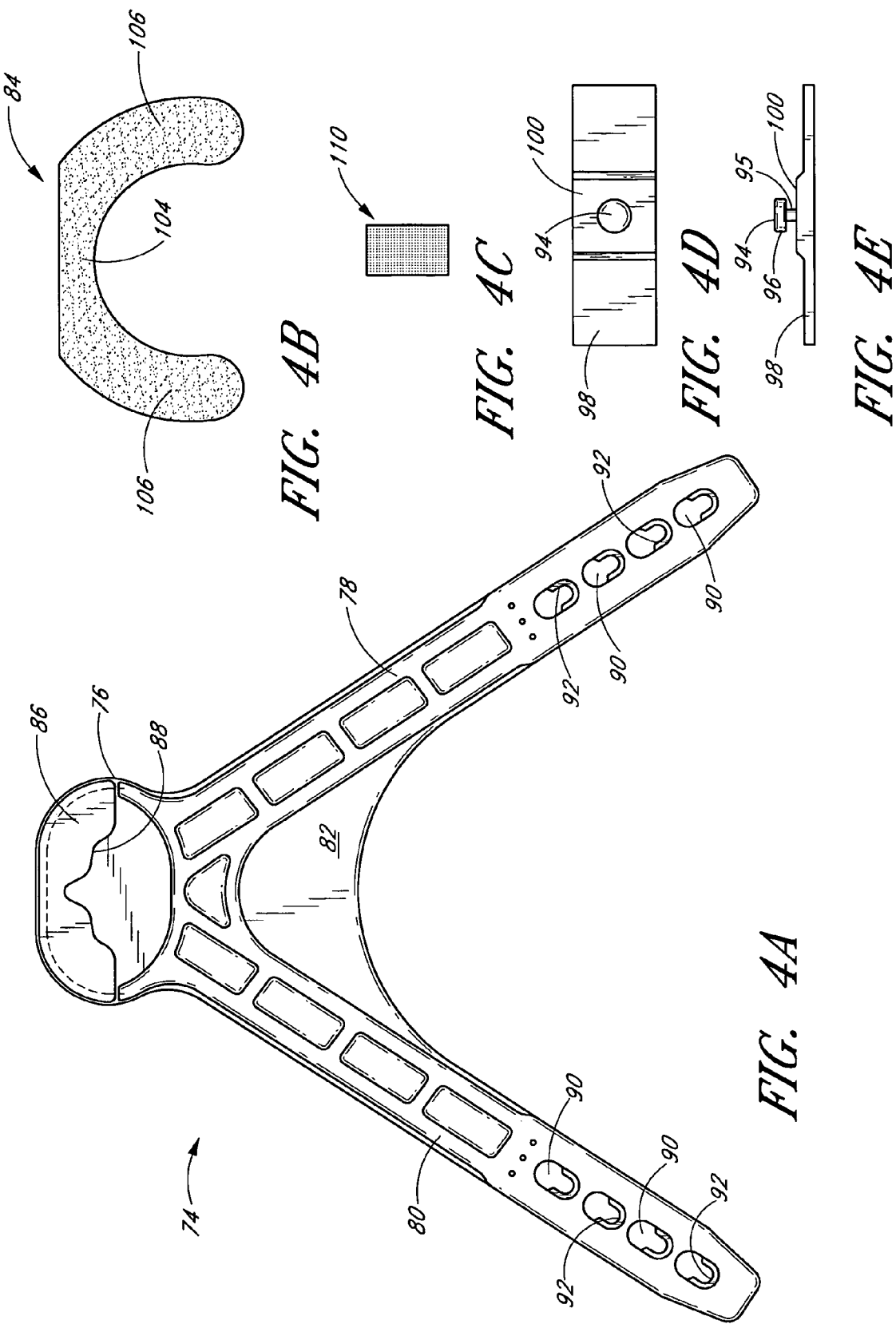
FIG. 4A is a top plan view of the patellofemoral support device of FIG. 3, which is one possible component of a conversion kit for converting a knee brace having a rigid frame into a knee brace that also provides patellofemoral support.
FIG. 4B is a top plan view of the buttress of the patellofemoral support device of FIG. 3, which is another possible component of a conversion kit for converting a knee brace having a rigid frame into a knee brace that also provides patellofemoral support.
FIG. 4C is a top plan view of a patch of hook material, which is another possible component of a conversion kit for converting a knee brace having a rigid frame into a knee brace that also provides patellofemoral support.
FIG. 4D is a top plan view of an anchoring button of the brace of FIG. 1, which is another possible component of a conversion kit for converting a knee brace having a rigid frame into a knee brace that also provides patellofemoral support.
FIG. 4E is a front elevational view of the anchoring button of FIG. 4D.
Figure 5:
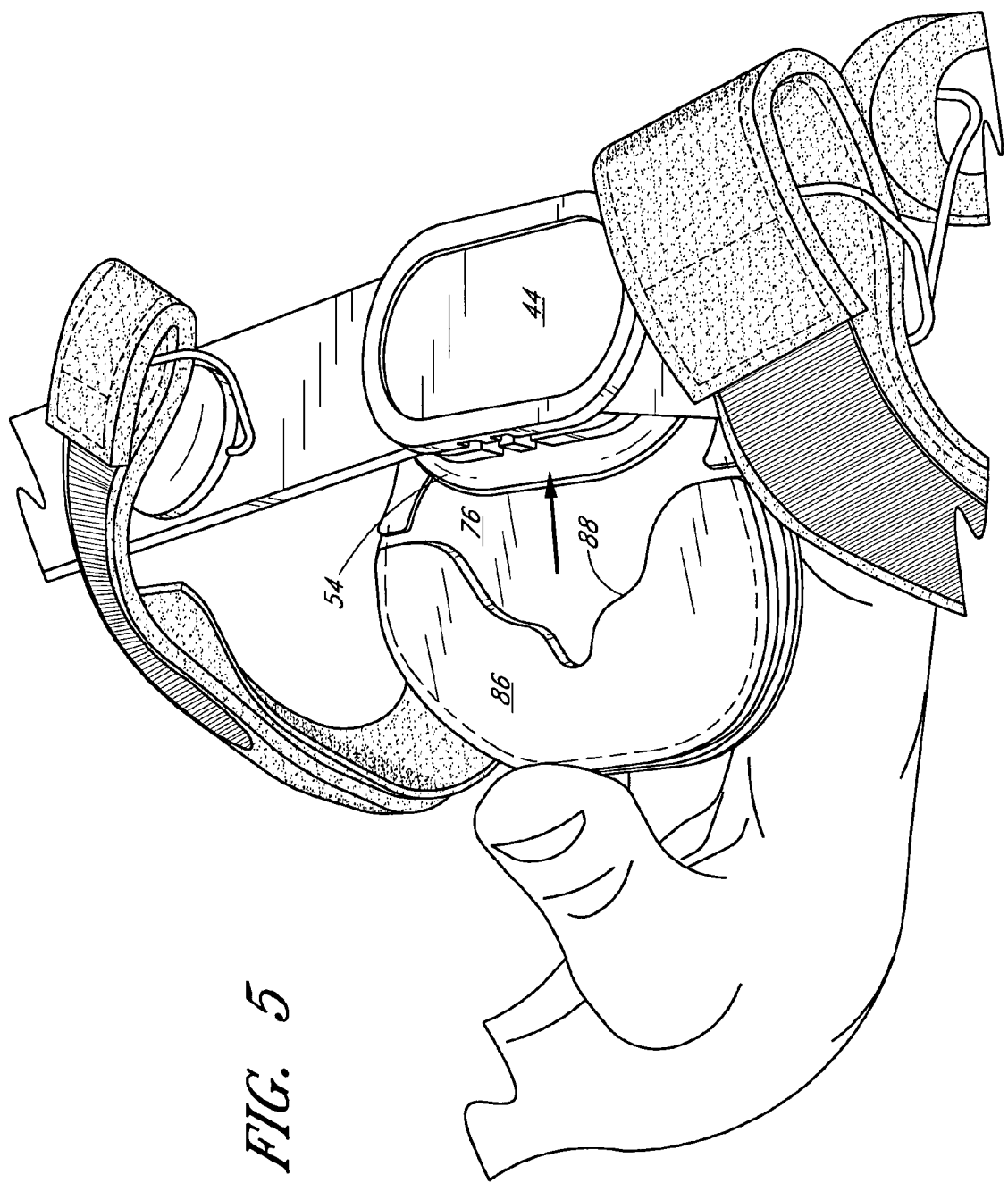
FIG. 5 is a detail view of the brace of FIG. 1 from a lower/lateral perspective, illustrating one method of attachment of the patellofemoral support device to a condyle shell of a lateral hinge of the brace.

The present brace 20 further includes a patellofemoral support device that is adapted to overlie the wearer's patella and provide relief for patellofemoral dysfunction. In the illustrated embodiment, the patellofemoral support device includes a patellar strap 74 that attaches to the lateral condylar shell 54 of the rigid frame 22 and extends across the wearer's knee. The strap 74, illustrated in FIG. 4A, is generally V-shaped when viewed in plan aspect, and includes a substantially oval-shaped base portion 76 at a vertex of the V. Those of ordinary skill in the art will appreciate that the base portion 76 need not be substantially oval-shaped, and could have virtually any shape. First and second arms 78, 80 extend away from the base portion 76 and form an angle of approximately 75° with respect to one another. A web 82 extends between the arms 78, 80 adjacent a base end of each.

The patellar strap 74 may be constructed of a flexible thermoplastic elastomer. Preferred thermoplastic elastomers include thermoplastic urethane and thermoplastic silicone. The patellar strap 74 could also be constructed of various naturally occurring materials having the desired properties of flexibility and elasticity, such as rubber. As shown in FIG. 3, an inner surface 83 of the patellar strap 74 that faces the wearer's leg may comprise a loop material, to facilitate the attachment of a buttress 84 thereto, as described in more detail below.

With reference to FIG. 4A, a plate 86 overlies a portion of an outside surface (facing away from the wearer) of the base portion 76. The plate 86 is shaped substantially as a half oval with an indentation along a side edge 88. The indented side edge 88 is unconnected to the base portion 76, while the remaining perimeter of the plate 86 is secured to the base portion 76, for example with stitching or adhesive. The plate 86 and base portion 76 thus form a space therebetween that is accessible along the indented side edge 88. In certain embodiments, the plate 86 may be constructed of a semi-rigid and resilient material, such as a plastic. Such a material generally holds a constant shape, but can be elastically deformed under digital pressure.

With reference to FIG. 4A, the space between the plate 86 and the base portion 76 of the patellar strap 74 is adapted to receive a portion of the lateral condylar shell 54. Sliding the base portion 76 in the direction of the arrow in FIG. 4A relative to the condylar shell 54 envelops a portion of the condylar shell 54 between the plate 86 and the base portion 76, and secures the patellar strap 74 to the condylar shell 54, as shown in FIGS. 2 and 3. Those of skill in the art will appreciate that the illustrated apparatus for securing the patellar strap 74 to the lateral side of the brace 20 is merely an example. The patellar strap 74 could, for example, be secured to the lateral condylar shell 54 or the lateral hinge 44 using conventional fastening members.

With reference to FIG. 4A, the first and second arms 78, 80 of the patellar strap 74 each include a plurality of spaced apertures 90. In the illustrated embodiment, each arm 78, 80 includes four evenly spaced apertures 90. However, as those of ordinary skill in the art will appreciate, fewer or more apertures 90 could be provided, and the apertures 90 need not be evenly spaced. Each aperture 90 is substantially oval, and houses an insert 92. Each insert 92 is substantially U-shaped, and is oriented within its respective aperture 90 such that an open end of the U points toward the base portion 76 of the patellar strap 74. With this configuration, each oval-shaped aperture 90 defines a relatively wider opening toward an end spaced from the insert 92, and a relatively narrower opening at an opposite end.

With reference to FIG. 1, the first and second arms 78, 80 extend across the anterior side of the brace 20 and are releasably securable to the medial side of the rigid frame 22. This configuration advantageously provides excellent leverage and applies a dynamic load to the wearer's patella, as discussed in detail below. With reference to FIGS. 1, 3, 6A and 6B, the medial calf upright 36 and the medial thigh upright 30 include apparatus for securing the first and second arms 78, 80. In the illustrated embodiment, upper and lower anchoring members are located on the medial thigh upright 30 and the medial calf upright 36, respectively. The illustrated anchoring members are shaped as tabs 94, however those of ordinary skill in the art will appreciate that the anchoring members could be of any configuration capable of anchoring the first and second arms 78, 80.

Figure 6A:
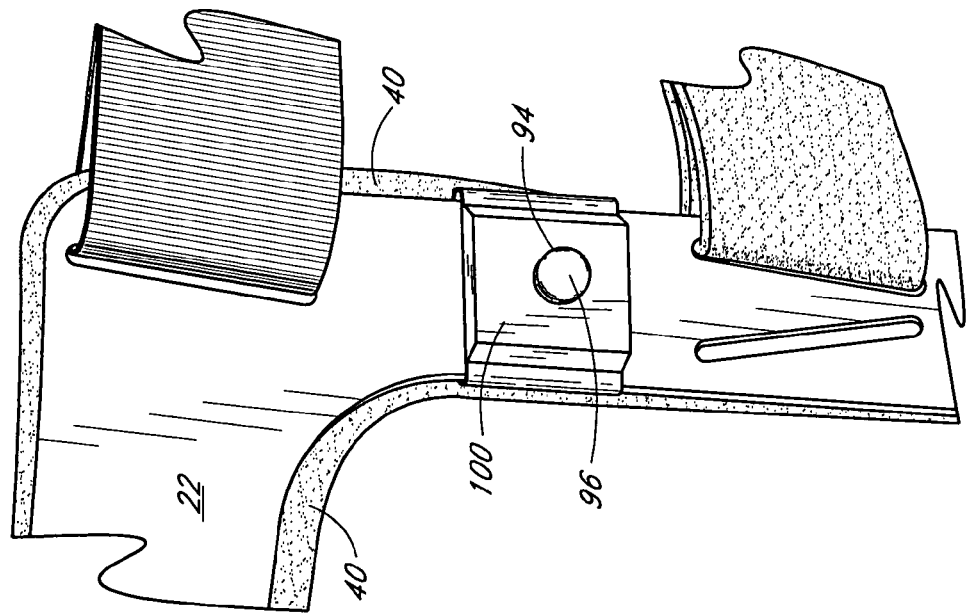
FIG. 6A is a detail view of the brace of FIG. 1 from a medial perspective, illustrating an anchoring button of the brace.

With reference to FIGS. 4E and 6A, each tab 94 includes a relatively narrow stem 95 and a relatively wide cap 96. The cap 96 is adapted to penetrate the wide portion of each aperture 90 in the first and second arms 78, 80, but is too wide to pass through the narrow portion thereof. Thus, to secure the first and second arms 78, 80 to the tabs 94, the wearer pulls the patellar strap 74 taut and inserts 92 the tab 94 through the wide portion of a desired aperture 90 and releases the strap 74. Tension in the strap 74 pulls the aperture 90 back across the tab 94, causing the stem 95 to slide toward the narrow end of the aperture 90 between the arms of the U-shaped insert 92. Since the cap 96 is too wide to fit through the insert 92, the tension in the strap 74 keeps the apertures 90 locked onto their respective tabs 94. Those of ordinary skill in the art will appreciate that the first and second arms 78, 80 need not include apertures 90. For example, the first and second arms could include hooks that would be adapted to mate with anchoring members having a different configuration from the tabs 94 shown.

Figure 6B:
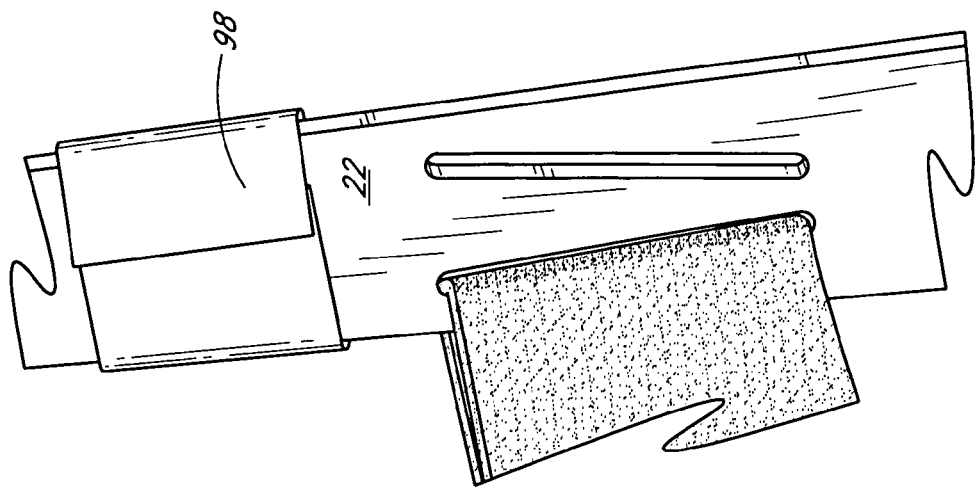
FIG. 6B is a detail view of the brace of FIG. 1 from a lateral perspective, illustrating an anchoring button of the brace.

With reference to FIGS. 6A and 6B, in one embodiment the tabs 94 are secured to the rigid frame 22 with adhesive. As shown in FIGS. 4D and 4E, each tab 94 is integrally formed with a short strip 98 of material. The strip 98 includes a relatively thick central portion 100 from which the tab 94 protrudes, and relatively thin portions extending from opposite edges of the central portion 100. An underside 102 of the strip 98 includes an adhesive. The central portion 100 is adapted to abut an outer surface (facing away from the wearer) of the frame 22, as shown in FIG. 6A. The thin portions are flexible, and wrap around the frame 22, as illustrated in FIG. 6B. The adhesive on the underside of the strip 98 secures the strip and tab 94 to the frame 22. Those of ordinary skill in the art will appreciate that the tabs 94 may be secured to the frame 22 in any of a variety of alternative fashions. For example, the tabs 94 may be formed integrally with the frame 22, or may be secured to the frame 22 with conventional fastening members, such as screws.

With reference to FIGS. 3 and 4B, certain embodiments of the present brace 20 include one or more buttresses 84 that are adapted to support the wearer's patella when the brace 20 is worn. The buttress 84 is substantially U-shaped and is releasably securable to the inside surface 83 of the patellar strap 74. For example, as described above the inside surface 83 may include loop material. A first surface (not visible) of the buttress 84 may include hook material, so that the buttress 84 is adapted to be releasably secured to the inside surface 83. Those of ordinary skill in the art will appreciate that alternative methods of releasably securing the buttress 84 to the patellar strap 74, such as snaps, could be used instead, and that the buttress 84 could be permanently secured to the patellar strap 74. However, if the buttress 84 can be removed and resecured to the patellar strap 74, then the buttress 84 can advantageously be oriented in whatever fashion is best suited to meet the patellar support needs of a particular wearer. For example, the buttress 84 can be adjusted in the superior/inferior direction, and the medial/lateral direction to provide proper fit and comfort for the wearer. Furthermore, a buttress having a particular thickness can be readily exchanged for one of a multitude of other buttresses having different thicknesses. The buttress could also be exchanged for a buttress having a variable, or tapering, thickness. Thus, a manufacturer can produce one brace 20 (perhaps in varying sizes) to treat a wide variety of patients, rather than having to produce specially designed braces to treat various forms of patellar dysfunction.

As shown in FIGS. 3 and 4B, the buttress 84 may be positioned on the patellar strap 74 such that a base 104 of the U-shaped buttress 84 abuts the lateral side of the wearer's patella when the patellar strap 74 is stretched across the anterior of the wearer's leg. Arms 106 of the buttress 84 surround the superior and inferior sides of the wearer's patella. In this configuration, the buttress 84 applies a medially directed force to the wearer's patella to treat patellar dysfunction. The patellar strap 74, which is preferably elastic, keeps the buttress 84 in contact with the patella. Tension in the patellar strap 74 applies force to the buttress 84 in the posterior and medial directions. Thus, as the wearer straightens his or her knee, the buttress 84 prevents the patella from subluxing laterally.

Advantageously, the buttress 84 abuts the wearer's patella directly. With reference to FIG. 3, the buttress 84 may include a right-angled edge 108 that provides a secure grip on the wearer's patella. However, because of the compressibility of the material used to construct the buttress 84, the buttress 84 conforms to the wearer's patella and provides a comfortable feel. Those of skill in the art will appreciate that the buttress 84 need not have a right-angled edge. For example, the buttress 84 could have a rounded edge.

In certain embodiments described above, the present knee brace 20 includes components that can readily be used as a conversion kit to convert a brace having a rigid frame into one that is also adapted to provide treatment for patellofemoral dysfunction. For example, FIGS. 4A-4E illustrate the components of one such conversion kit, including the patellar strap 74, at least one optional buttress 84, first and second tabs 94, and a plurality of optional patches of hook fastener 110. Those of ordinary skill in the art will appreciate that a wearer may convert a brace having a rigid frame into one that is also adapted to provide treatment for patellofemoral dysfunction using only the patellar strap 74 and the first and second tabs 94. The components shown in FIGS. 4B and 4C are merely optional.

Figure 7:
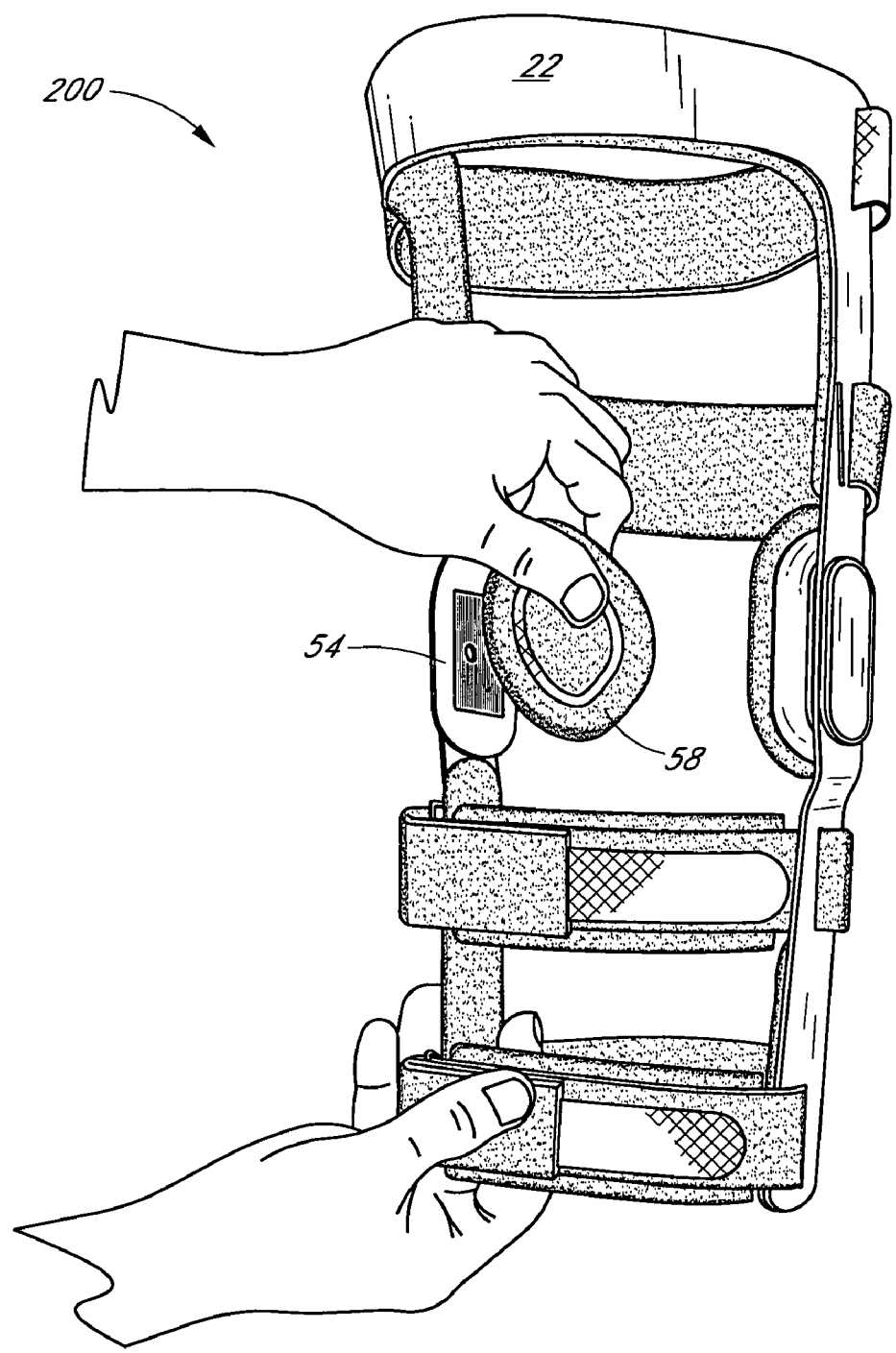
FIG. 7 is a front/medial perspective view of a knee brace having a rigid frame, illustrating one step in a method of converting the brace into a knee brace having a rigid frame and patellofemoral support.

FIG. 7 illustrates a knee brace 200 having a rigid frame 22. Braces similar to the illustrated brace are commonly used to protect and support a wearer's knee. For example, the illustrated brace 200 is configured to support the knee ligaments and prevent injury thereto. The brace 200 includes no apparatus, however, for supporting a wearer's patella. Advantageously, the conversion kit shown in FIGS. 4A-4E can be used to easily and inexpensively convert the brace 200 into a brace that supports the patella. For example, a certain segment of the population currently wears a brace like the brace 200. A certain percentage of these wearers may at some later date require patella support in addition to the support and protection provided by the brace 200. By using the present conversion kit in the manner described below, these brace wearers need not scrap their current brace 200 and replace it with another brace that provides both ligament support and patella support. Similarly, these brace wearers need not attempt to combine their current brace with a separate patellofemoral brace that may not be compatible with their current brace, or that may cause their current brace to fit improperly.

Figure 8:
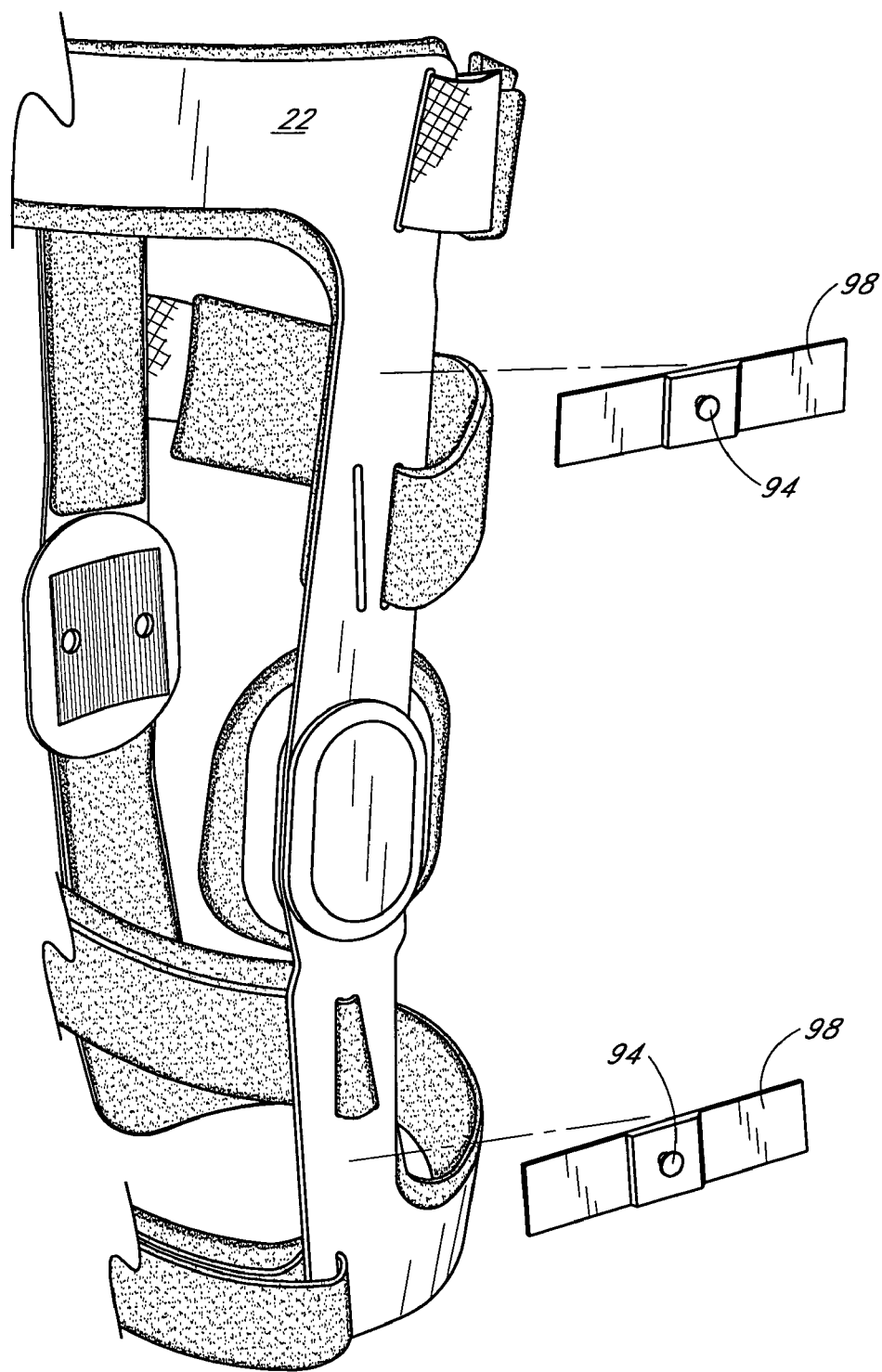
FIG. 8 is a front/medial perspective view of the knee brace of FIG. 7, illustrating another step in a method of converting the brace into a knee brace having a rigid frame and patellofemoral support.
Figure 9:
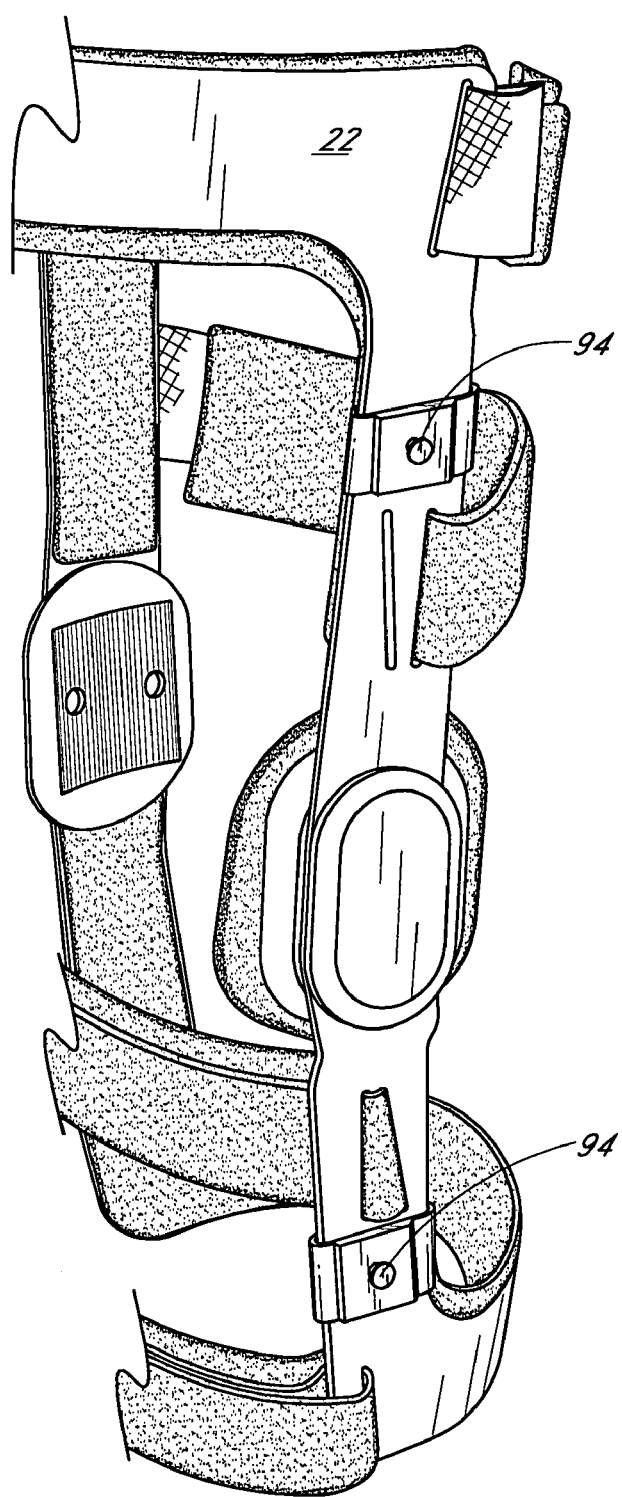
FIG. 9 is a front/medial perspective view of the knee brace of FIG. 7, illustrating another step in a method of converting the brace into a knee brace having a rigid frame and patellofemoral support.

To convert a brace 200 using the kit, the wearer (or anyone performing the conversion) first removes the lateral condylar pad (if one is provided) from the lateral condylar shell 54, as shown in FIG. 7. Next, the wearer secures the first and second tabs 94 to the medial side of the frame 22, as shown in FIGS. 8 and 9. In one embodiment, the tabs 94 are secured to the frame 22 with adhesive. For example, the underside 102 of each strip 98 may include pre-applied adhesive protected by a paper backing (not shown). The wearer would thus remove the paper backing, press the strip 98 against the frame 22 such that the tab 94 faces away from the wearer, and wrap the strip 98 around the opposite side of the frame 22, securing the ends thereto, as shown in FIGS. 6A and 6B. If the frame 22 includes padding 40 or any other potential obstructions on its inner surfaces (facing the wearer), the wearer may temporarily remove these obstructions in order to secure the tabs 94 to the frame 22.

Figure 10:
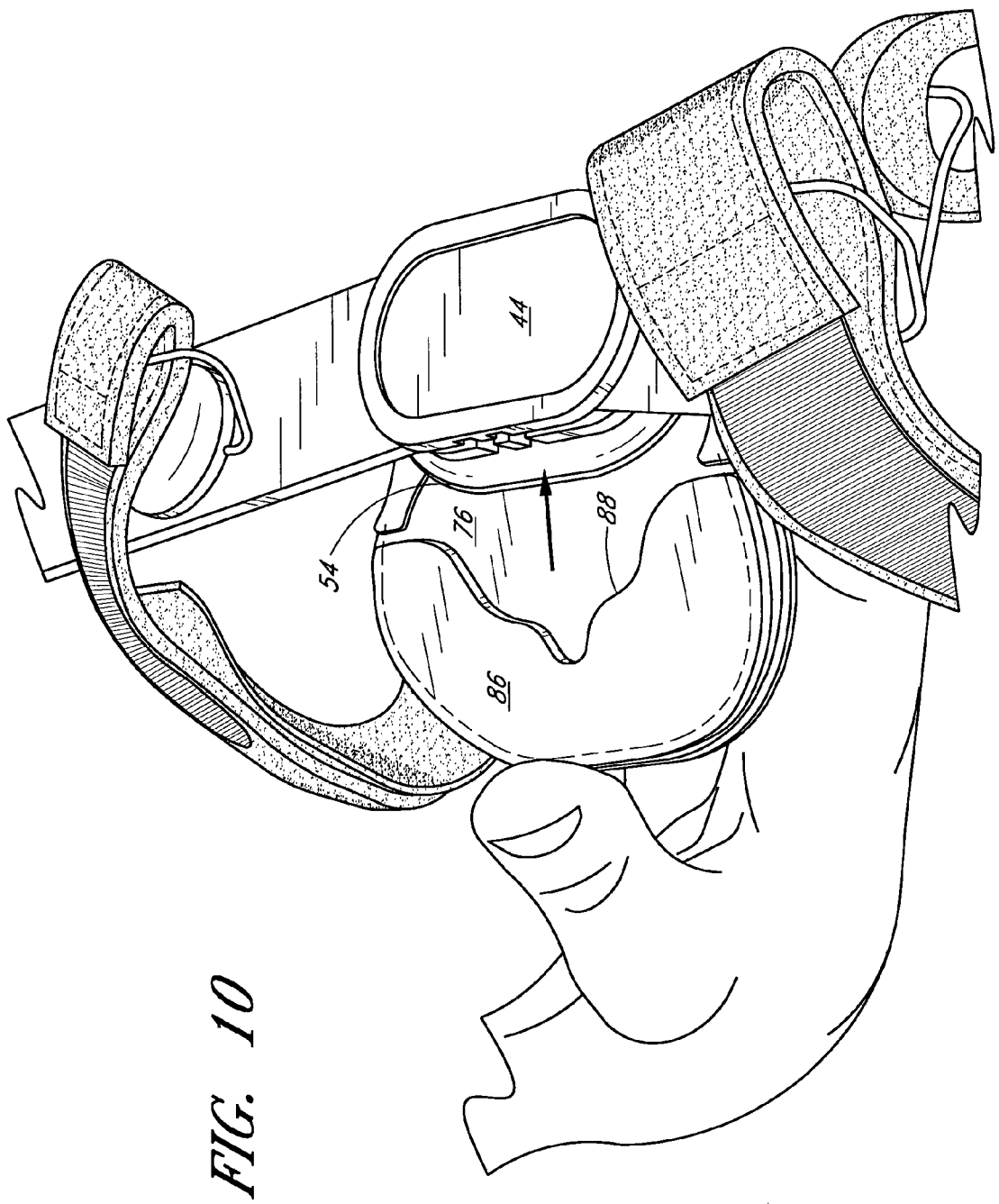
FIG. 10 is a lower/lateral perspective view of the knee brace of FIG. 7, illustrating another step in a method of converting the brace into a knee brace having a rigid frame and patellofemoral support.
Figure 11:
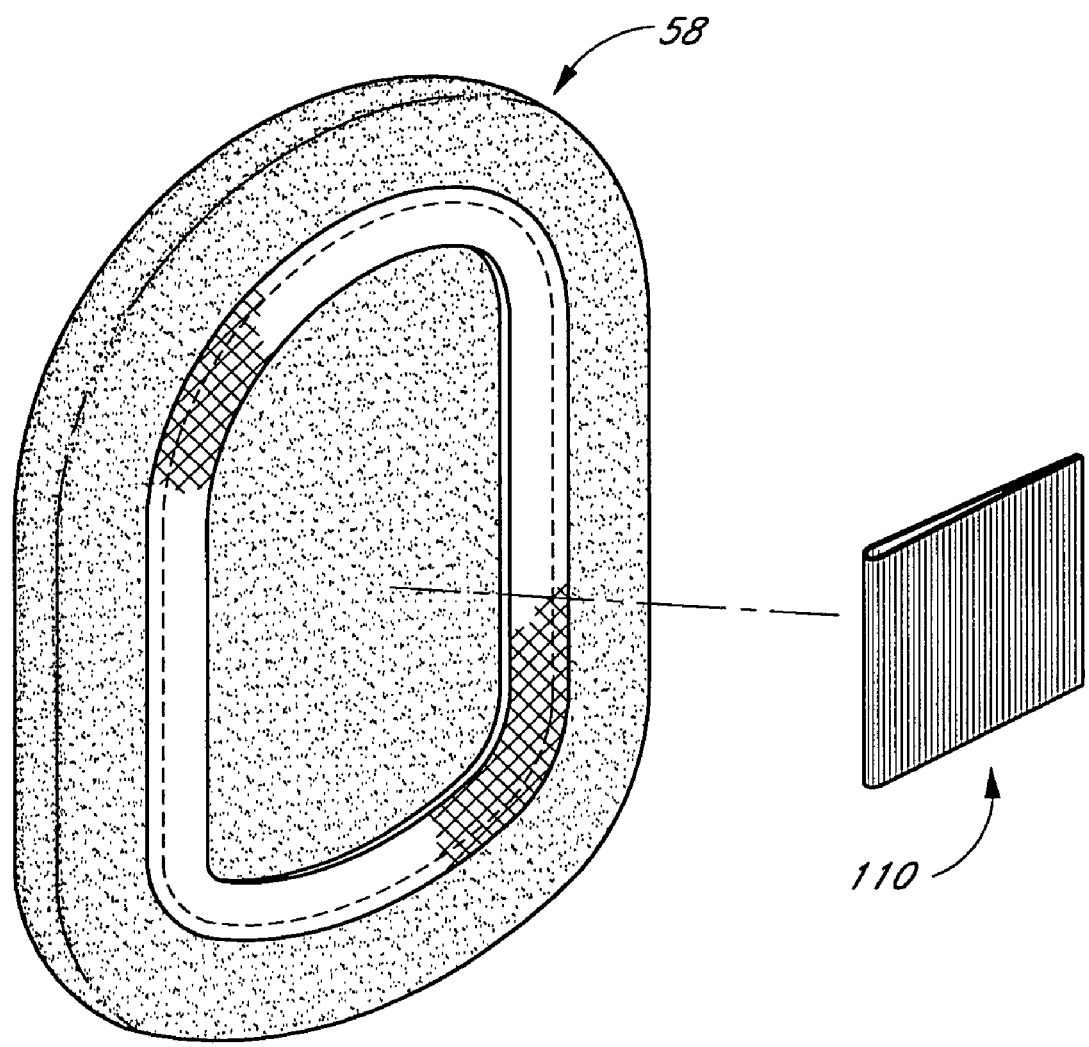
FIG. 11 is a lateral condyle pad for use in the brace of FIG. 1, illustrating a step of securing a patch of hook fastener to the pad.
Figure 12:
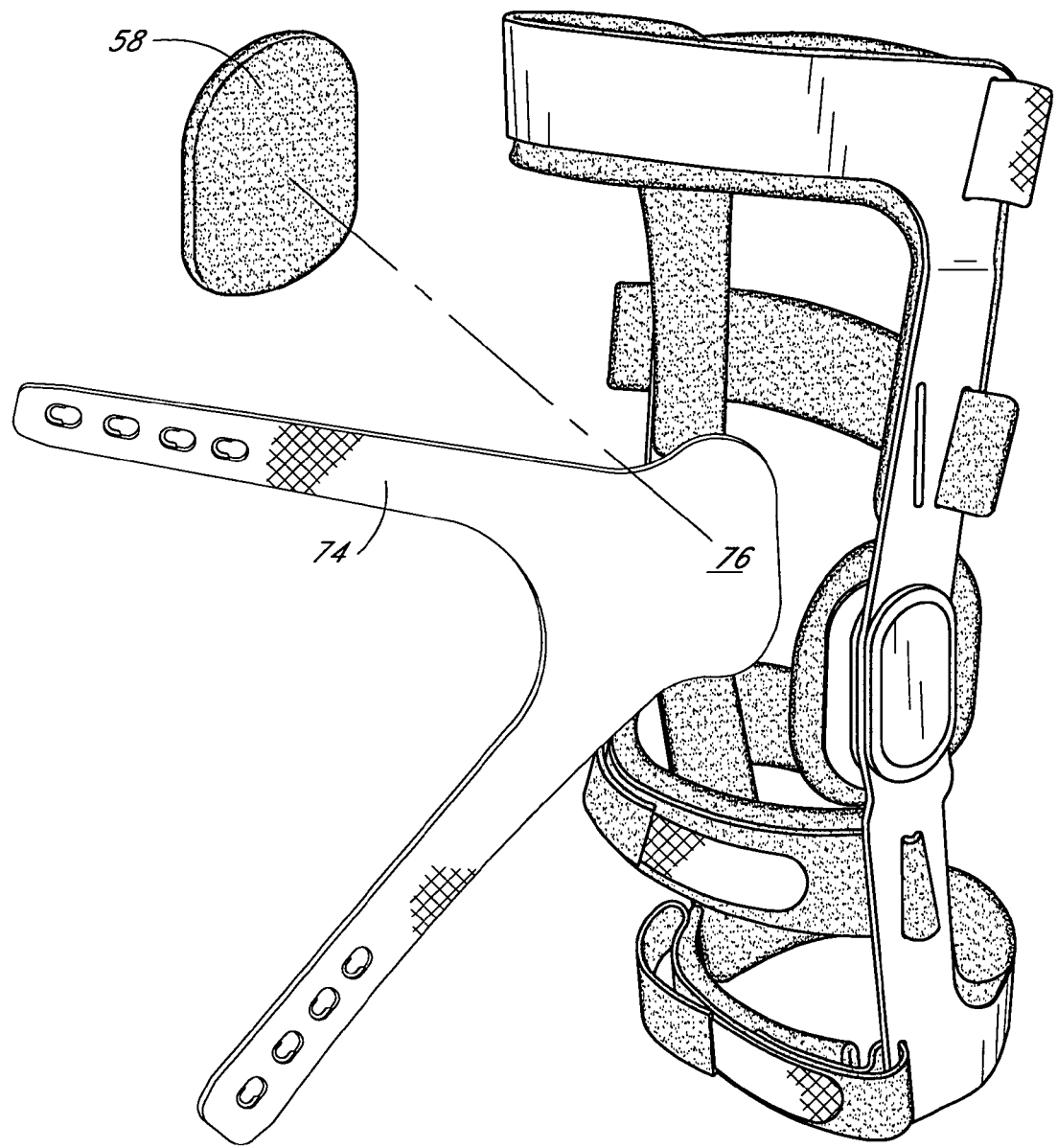
FIG. 12 is a front/medial perspective view of the knee brace of FIG. 7, illustrating another step in a method of converting the brace into a knee brace having a rigid frame and patellofemoral support.

The wearer next slides the lateral condylar shell 54 into the envelope formed by the plate 86 and the base portion 76 of the patellar strap 74, as described above and as illustrated in FIG. 10. The wearer may then optionally apply a lateral condylar pad 58 over the base portion 76, as shown in FIG. 12. Before doing so, the wearer may apply one of the patches of hook material 110 (FIG. 4C) to the pad 58. The patch of hook material 110 may have hook material on each of its opposite facing surfaces. The hook material mates with the loop material on the base portion 76 and the lateral condylar pad 58 to help retain the pad 58 on the base portion 76. In one embodiment, the patch of hook material 110 may have hook material on only one of its surfaces, and adhesive on the opposite surface. A patch having such a configuration may be folded in half so that adhesive surfaces contact and adhere to one another. The patch then has hook material on each of its opposite facing surfaces.

Figure 13:
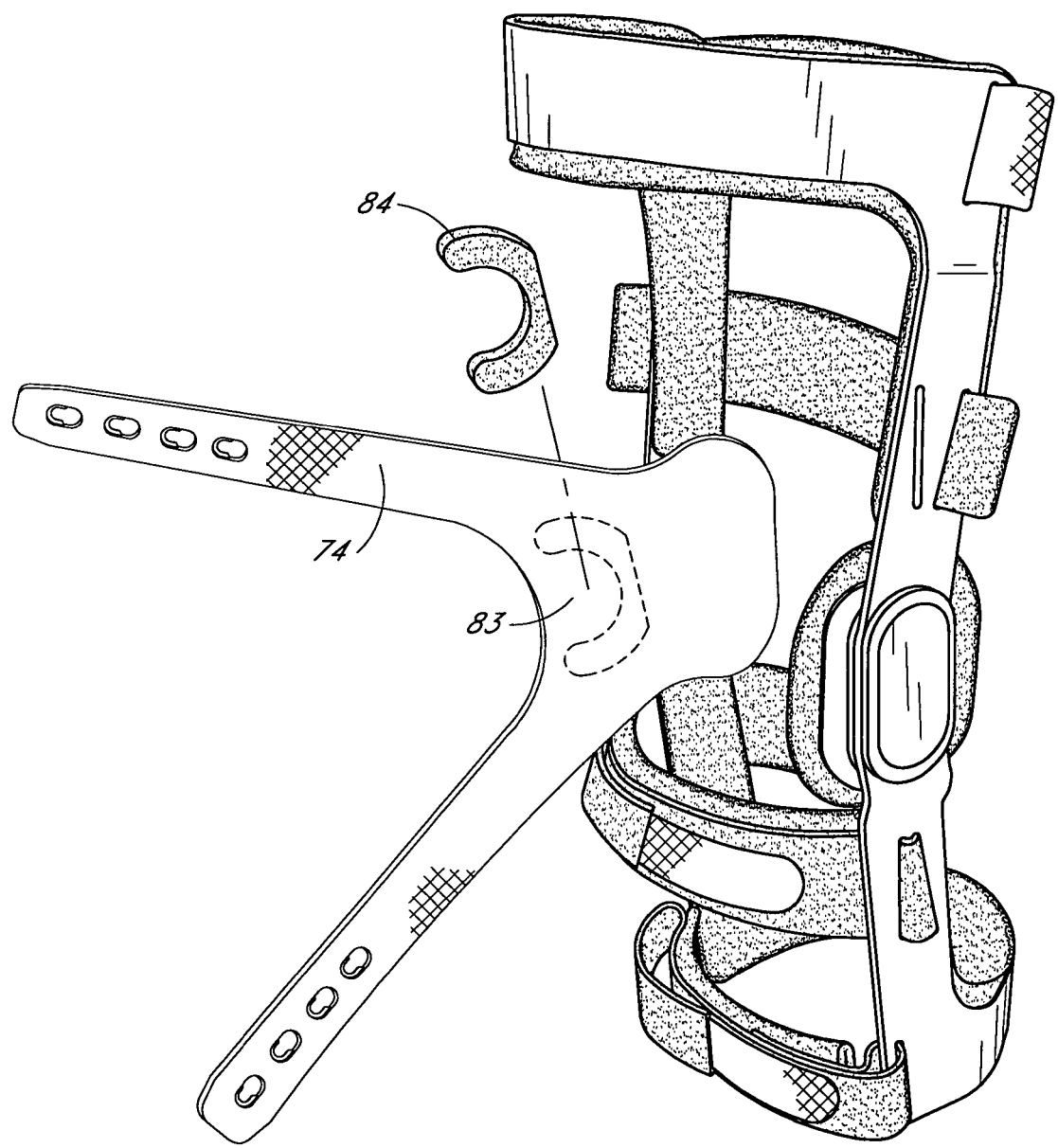
FIG. 13 is a front/medial perspective view of the knee brace of FIG. 7, illustrating another step in a method of converting the brace into a knee brace having a rigid frame and patellofemoral support.

The wearer next applies the buttress 84 to the inner surface 83 (facing the wearer) of the patellar strap 74, as illustrated in FIG. 13. The conversion kit may include buttresses of different sizes, thicknesses, shapes, etc. to suit a variety of different wearers. If the wearer requires support for the lateral side of his or her patella, then the buttress may be positioned on the patellar strap 74 such that it abuts the lateral, superior and inferior sides of the patella when the brace 20 is worn.

To apply the embodiments of the present brace 20 to his or her knee, the wearer first unfastens all, or substantially all, of the straps 62 and steps into the brace 20 so that the hinges 42, 44 are located adjacent the medial and lateral sides of his or her knee, as shown in FIGS. 1 and 2. The wearer then tightens the straps 62 one at a time until each provides a snug fit about his or her thigh and calf. Grasping the first and second arms 78, 80, the wearer pulls the patellar strap 74 across the anterior of his or her leg and secures the apertures 90 in the arms about the tabs 94 on the brace frame 22, as shown in FIG. 1. The wearer pulls the strap 74 to a snug but comfortable fit that allows the buttress 84 to apply its supporting force to the patella. If the fit is too loose or too snug, the wearer can adjust as necessary. Further, if the position of the buttress creates discomfort or results in inadequate patellar support, the wearer can detach the arms 78, 80 from the tabs 94 and adjust the position of the buttress relative to the patellar strap 74. As discussed above, the buttress 84 can advantageously be adjusted in both the medial/lateral direction and the superior/inferior direction. When the proper fit is achieved, loose ends of the first and second arms 78, 80 can be trimmed so as not to interfere with the wearer as he or she moves about. The wearer may trim the arms with a scissors, for example.

When the brace 20 is worn as illustrated in FIGS. 1 and 2, it advantageously provides both external support for ligament instabilities, and protection against patellofemoral dysfunction. The patellar strap 74 advantageously provides anterior loading to the wearer's patella to support patellar malalignments such as patella alta, patella baja, tilt and glide, and to protect against patellar subluxation and dislocation. The patellar strap 74 further advantageously provides a dynamic load to the wearer's patella through the range of motion. The first and second straps 78, 80 attach to the medial side of the rigid frame 22. This portion of the rigid frame 22 moves relative to the lateral hinge 44 as the wearer's knee flexes and extends, thereby increasing the tension in the patellar strap 74 as the wearer's knee extends, and decreasing the tension in the patellar strap 74 as the wearer's knee flexes.

The configuration of the patellar strap 74 and the rigid frame 22 also provides the brace 20 with excellent leverage. Again, the first and second straps 78, 80 attach to the medial side of the rigid frame 22, and the base of the patellar strap 74 (the base portion 76) attaches to the lateral condylar shell 54. Thus, the patellar strap 74 is secured at both ends to the rigid frame 22, so that neither end of the patellar strap 74 can shift as the wearer moves about. The secure anchoring of both ends of the patellar strap 74 allows the strap 62 to provide excellent leverage against the wearer's patella. Further, because the arms 78, 80 wrap around the anterior surface of the wearer's leg and connect to the medial side of the rigid frame 22, the arms actually pull the web 82 (FIG. 4A) and the portions of the strap 62 adjacent the web 82 in a distal direction as well as a medial direction. These distal and medial force components applied to the patella provide excellent leverage for supporting the patella.

Those of ordinary skill in the art will appreciate that in certain other embodiments the rigid frame 22 of the present brace 20 may be configured to provide relief from pain caused by osteoarthritis. For example, the brace 20 may be configured to apply a medially or laterally directed force to the wearer's knee to compensate for cartilage that has degenerated due to unicompartmental osteoarthritis.

The embodiments of the knee brace 20 described herein advantageously combine the ability to treat, for example, osteoarthritis or ligament instability with the ability to treat patellofemoral dysfunction. The brace 20 also advantageously combines a rigid frame 22 with flexible strapping that supports the wearer's patella. The flexible strapping is incrementally adjustable to provide proper fit, functionality and comfort. In certain embodiments, the brace 20 comprises a conversion kit that enables a brace wearer to convert a rigid brace 200 into one that also provides patellofemoral support. The conversion kit thus provides a relatively inexpensive modification to an existing brace 200, so that a brace wearer need not go out and purchase a brand new brace.

The embodiments of the present knee brace 20 described above are configured to support the lateral side of a wearer's patella. Thus, these embodiments are adapted to treat, for example, lateral patellar subluxation. However, many wearers will require a brace that is configured to support the medial side of the patella. Accordingly, those of ordinary skill in the art will appreciate that the configurations of the embodiments described herein could be reversed in order to provide a brace that is configured to support the medial side of a wearer's patella.

SCOPE OF THE INVENTION

The above presents a description of the best mode contemplated for carrying out the present knee brace having a rigid frame and patellofemoral support, and of the manner and process of making and using it, in such full, clear, concise, and exact terms as to enable any person skilled in the art to which it pertains to make and use this knee brace. This knee brace is, however, susceptible to modifications and alternate constructions from that discussed above that are fully equivalent. Consequently, this knee brace is not limited to the particular embodiments disclosed. On the contrary, this knee brace covers all modifications and alternate constructions coming within the spirit and scope of the knee brace as generally expressed by the following claims, which particularly point out and distinctly claim the subject matter of the knee brace.

What is claimed is:

1. A knee brace for supporting or protecting a wearer's knee, while also providing support to the wearer's patella comprising:
    a rigid brace frame including a rigid thigh cuff, a rigid calf cuff, and at least a first hinge pivotably securing the thigh cuff to the calf cuff;
    a patellar strap having a base portion and at least a first elongate arm extending from the base portion, wherein the base portion is operatively secured to the rigid brace frame along a medial side or a lateral side thereof, and the arm extends across an anterior portion of the rigid brace frame and is secured to the rigid brace frame along the medial side or the lateral side thereof, opposite the base portion, and wherein the base portion is operatively secured to the hinge; and
    a plate secured to the base portion, and wherein a space between the plate and the base portion receives a condyle shell of the hinge, thereby releasably securing the base portion to the hinge.

2. The knee brace of claim 1, wherein the hinge is located on the lateral side of the rigid brace frame.

3. The knee brace of claim 1, wherein the rigid brace frame includes at least a first anchoring member configured to receive the first arm of the strap, and wherein the first arm is releasably securable to the first anchoring member.

4. The knee brace of claim 3, wherein the first anchoring member comprises a tab that is removably receivable within at least a first aperture in the first arm of the strap.

5. The knee brace of claim 1, wherein the base portion is releasably secured to the hinge.

6. A knee brace for supporting and/or protecting a wearer's knee, while also providing support to the wearer's patella, comprising:
    a rigid brace frame including a rigid thigh cuff, a rigid calf cuff, and at least a first hinge pivotably securing the thigh cuff to the calf cuff; and
    a patellar strap having a base portion and at least a first elongate arm extending from the base portion, the first elongate arm including an aperture with an insert that receives a fastener;
    wherein the base portion is operatively secured to the rigid brace frame along a medial side or a lateral side thereof, and the arm extends across an anterior portion of the rigid brace frame and is secured to the rigid brace frame along the medial side or the lateral side thereof, opposite the base portion.

7. The knee brace of claim 6, wherein the patellar strap includes a second arm extending from the base portion, such that the strap has a substantially V-shaped configuration when laid flat.

8. The knee brace of claim 6, wherein the insert includes an open end oriented towards the base portion of the patellar strap.

9. The knee brace of claim 6, wherein the aperture defines a relatively wider opening towards an end spaced away from the insert.

10. The knee brace of claim 6, wherein the insert is substantially U-shaped.

11. A conversion kit configured to provide patellofemoral support to a knee of a wearer, the kit comprising:
    a patellar strap having a base portion and at least a first elongate arm extending therefrom; and
    at least a first anchoring member configured to releasably secure the first arm of the patellar strap adjacent a knee of a wearer;
    wherein the first anchoring member is secured along a rigid frame of a knee brace at a site selected by the wearer.

12. The conversion kit of claim 11, wherein the first arm includes at least a first aperture.

13. The conversion kit of claim 12, wherein the first anchoring member comprises a relatively narrow stem and a relatively wide cap extending from the stem, and the first aperture is configured to releasably receive the first anchoring member.

14. The conversion kit of claim 11, further comprising a plate secured to the base portion, a space between the base portion and the plate being configured to releasably receive a condylar shell of a knee brace.

15. The conversion kit of claim 11, further comprising a buttress configured to be releasably secured to the patellar strap.

16. A patellar strap, comprising:
    a base portion;
    a plate overlying at least part of the base portion, the plate being secured to the base portion such that at least a segment of a perimeter of the plate is unsecured;
    at least a first elongate arm extending from the base portion; and
    a second elongate arm extending from the base portion, such that the strap has a substantially V-shaped configuration when laid flat;
    wherein a space between the base portion and the plate is accessible along the unsecured perimeter segment, and is configured to receive a portion of a knee brace to releasably secure the strap thereto.

17. The patellar strap of claim 16, wherein the space between the base portion and the plate is configured to receive a condyle shell of a hinge of a knee brace.

18. The patellar strap of claim 16, wherein the base portion is shaped substantially as an oval.

19. The patellar strap of claim 16, wherein the plate is shaped substantially as a half oval.

20. The patellar strap of claim 16, wherein the first arm includes at least one aperture.

21. The patellar strap of claim 16, wherein at least a portion of the strap is constructed of a thermoplastic elastomer.

22. A method of converting a knee brace having a rigid brace frame into a knee brace capable of providing patellofemoral support to a knee of a wearer, the method comprising the steps of:
   securing a base portion of a patellar strap to the frame along a medial side or a lateral side thereof, the strap including at least a first elongate arm;
   securing at least a first anchoring member to the medial side or the lateral side of the frame, opposite the base portion; and
   securing a buttress to the patellar strap,
   wherein the first anchoring member is secured to the rigid brace frame using an adhesive.

23. A method of converting a knee brace having a rigid brace frame into a knee brace capable of providing patellofemoral support to a knee of a wearer, the method comprising the steps of:
   securing a base portion of a patellar strap to the frame along a medial side or a lateral side thereof, the strap including at least a first elongate arm;
   securing at least a first anchoring member along the rigid frame at a site selected by the wearer; and
   securing a buttress to the patellar strap.

24. The method of claim 23, wherein the base portion of the patellar strap is operatively secured to a hinge of the rigid brace frame.

25. The method of claim 23, further comprising the step of releasably securing the first arm to the first anchoring member.

26. The method of claim 23, wherein the step of securing the first anchoring member comprises securing the first anchoring member along the medial side or the lateral side of the frame opposite the base portion.

* * * * *